US006187890B1

(12) United States Patent
Fehn et al.

(10) Patent No.: US 6,187,890 B1
(45) Date of Patent: Feb. 13, 2001

(54) CURABLE ORGANOPOLYSILOXANE COMPOSITIONS

(75) Inventors: Armin Fehn, Emmerting; Frank Achenbach, Simbach/Inn; Stefan Dietl, Burghausen, all of (DE)

(73) Assignee: Wacker-Chemie GmbH, Munich (DE)

( * ) Notice: Under 35 U.S.C. 154(b), the term of this patent shall be extended for 0 days.

(21) Appl. No.: 09/374,430

(22) Filed: Aug. 13, 1999

(30) Foreign Application Priority Data

Aug. 20, 1998  (DE) .............................................. 198 37 855

(51) Int. Cl.$^7$ ................................................... C08G 77/08
(52) U.S. Cl. ............................. 528/15; 528/23; 502/152; 502/155; 502/213; 525/478; 525/479; 987/10
(58) Field of Search ..................... 502/152, 155, 502/213; 528/15, 23; 525/478, 479; 987/10

(56) References Cited

U.S. PATENT DOCUMENTS

| 3,188,300 | * | 6/1965 | Chalk . |
| 3,532,649 | * | 10/1970 | Smith et al. . |
| 4,256,616 | | 3/1981 | Hatanaka et al. . |
| 4,329,275 | | 5/1982 | Hatanaka et al. . |
| 4,584,361 | * | 4/1986 | Janik et al. . |
| 4,631,310 | * | 12/1986 | Chandra et al. . |
| 4,645,815 | | 2/1987 | Lewis . |
| 5,270,422 | * | 12/1993 | Hoag et al. . |
| 5,328,974 | | 7/1994 | McAfee et al. . |
| 5,561,231 | | 10/1996 | Dauth et al. . |
| 5,629,399 | * | 5/1997 | Juen et al. . |
| 5,703,190 | * | 12/1997 | Dauth et al. . |
| 6,100,348 | * | 8/2000 | Dauth et al. . |

FOREIGN PATENT DOCUMENTS

| 2 259 255 A1 | 1/1998 | (CA) . |
| 36 35 236 A1 | 5/1987 | (DE) . |
| 0 182 611 A2 | 5/1986 | (EP) . |
| 0 363 006 A2 | 4/1990 | (EP) . |
| 0 583 159 A2 | 2/1994 | (EP) . |
| 0 638 604 A1 | 2/1995 | (EP) . |
| 2 750 349 A1 | 1/1998 | (FR) . |

OTHER PUBLICATIONS

H.D. Empsall, B.L. Shaw, A.J. Stringer, Journal of Organometallic Chemistry, (1975), 94, pp. 131–138.
M.V. Russo, A. Furlani, Journal of Organometallic Chemistry, (1979), 165, pp. 101–105.
I. Collamati, A. Furlani, Journal of Organometallic Chemistry, (1969), 17, pp. 457–461.
A. Furlani, P. Bicev, M.V. Russo, P. Carusi, Journal of Organometallic Chemistry, (1971), 29, pp. 321–327.
K. Sonogashira et al., Journal of Organometallic Chemistry, (1978), 145, pp. 101–108.
A. Furlani, P. Carusi, M.V. Russo, Journal of Organometallic Chemistry, (1976), 116, pp. 113–122.
A. Furlani et al., J. Chem. Soc. Dalton Trans., (1984), pp. 2197–2206.
K. Sonogashira, S. Takahashi, N. Hagihara, Macromolecules, (1977), pp. 879–880.
S. Kotani, K. Shiina, K. Sonogashira, Applied Organometallic Chemistry, (1991), vol. 5, pp. 417–425.
J.F. Almeida, A. Pidcock, Journal of Organometallic Chemistry, (1981), 209, pp. 415–423.
J. Fornies et al., Organometallics, (1992), 11, pp. 2873–2883.

* cited by examiner

Primary Examiner—Robert Dawson
Assistant Examiner—Marc S. Zimmer
(74) Attorney, Agent, or Firm—Brooks & Kushman P.C.

(57) ABSTRACT

Curable organopolysiloxane compositions comprising a platinum catalyst selected from the group consisting of

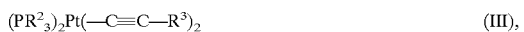

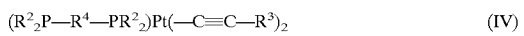

and

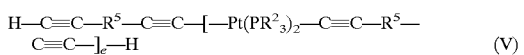

where $R^2$, $R^3$, $R^4$, $R^5$ and e are as defined in claim 1.

16 Claims, No Drawings

CURABLE ORGANOPOLYSILOXANE COMPOSITIONS

TECHNICAL FIELD

The present invention relates to silicone compositions which crosslink thermally by hydrosilylation, their preparation and their use.

BACKGROUND ART

Addition-crosslinking silicone compositions crosslink by reaction of aliphatically unsaturated groups with Si-bonded hydrogen (hydrosilylation) in the presence of a catalyst, typically a platinum compound. Owing to the fact that the crosslinking reaction commences when the essential constituents are simultaneously present, addition-crosslinking silicone compositions have hitherto been prepared virtually exclusively as two-component formulations, with the composition of the individual components being such that all three essential constituents are present together only after the components are mixed. Customarily, one of the components comprises the alkenyl-functional polyorganosiloxane and the platinum catalyst while the other component comprises the SiH-functional crosslinker, if desired in combination with the alkenyl-functional polyorganosiloxane. After mixing the individual components, complete curing to form the silicone elastomer can be carried out at room temperature, but it is customarily carried out at elevated temperature.

The two-component system for addition-crosslinking silicone compositions is associated with numerous disadvantages, for instance logistics, the high risk of contamination by traces of platinum and the presence of an additional mixing step. Although mixing of the components does give a ready-to-use composition, this composition has only a very limited pot life at room temperature. This not only makes immediate processing necessary but also requires frequent cleaning of the stock vessels, metering units, processing machines, etc., since any material remaining, for example as a result of backmixing or sticking to the walls, ultimately gels.

Owing to the disadvantages of such two-component compositions, there has been no lack of attempts to make addition-crosslinking silicone compositions available as one-component formulations. Since in the case of a one-component system all constituents necessary for crosslinking are present simultaneously, the problem is essentially to suppress premature commencement of the crosslinking reaction which normally proceeds even at room temperature. Possible ways of setting (increasing) the pot life of an addition-crosslinking composition in a targeted way have been known for some time, e.g. by the use of inhibitors which are capable of considerably reducing the activity of the platinum catalyst at room temperature, for example phosphorus compounds in combination with peroxides as described in U.S. Pat. No. 4,329,275 or azodicarbonyl compounds as described in EP-A-490 523. Although choice of type and amount of such inhibitors makes it possible to increase the pot life to any desired extent, an adverse effect on the crosslinking behavior is unavoidably associated with this increasing pot life. This is particularly true when the pot life is extended to a number of months by means of high inhibitor contents. In such cases, increased start temperature and undesirable crosslinking behavior ranging from a low crosslinking rate to insufficient crosslinking, are the result.

A further, fundamentally different technique is encapsulation of the platinum catalyst in a finely divided material which releases the platinum only at elevated temperature. This can be achieved, for example, by microencapsulation of the platinum catalyst in a thermoplastic silicone resin or an organic thermoplastic as described, for example, in EP-A-363 006. However, such techniques are relatively complicated.

A third possibility is to select, as catalyst, specific platinum complexes whose activity is such that the hydrosilylation reaction proceeds sufficiently rapidly at elevated temperature but at room temperature proceeds only to such a small degree that pot lives of a number of months are achieved. Addition-crosslinking compositions comprising such platinum complexes have been described, for example, in EP-A-583 159 and DE-A-36 35 236. Although the compositions described have significantly improved pot lives at sometimes sufficiently high crosslinking rates, there continues to be a need to improve the pot life and crosslinking rate of one-component, addition-crosslinking compositions by means of better platinum catalysts without having to accept the abovementioned disadvantages. This object is achieved by the present invention.

SUMMARY OF THE INVENTION

The present invention provides curable organopolysiloxane compositions comprising (A) compounds having radicals containing aliphatic carbon—carbon multiple bonds, (B) organopolysiloxanes containing Si-bonded hydrogen atoms, or, in place of (A) and (B), (C) organopolysiloxanes having SiC-bonded radicals containing aliphatic carbon—carbon multiple bonds and Si-bonded hydrogen atoms, and (D) a platinum catalyst exhibiting little or no activity at low temperatures, and excellent crosslinking behavior at elevated temperatures as hereinafter described.

For the purposes of the present invention, the term organopolysiloxanes includes polymeric, oligomeric and dimeric siloxanes.

DESCRIPTION OF THE PREFERRED EMBODIMENTS

The present invention provides curable organopolysiloxane compositions comprising (A) compounds having radicals containing aliphatic carbon—carbon multiple bonds, (B) organopolysiloxanes containing Si-bonded hydrogen atoms, or, in place of (A) and (B), (C) organopolysiloxanes having SiC-bonded radicals containing aliphatic carbon—carbon multiple bonds and Si-bonded hydrogen atoms, and (D) a platinum catalyst selected from the group consisting of

  (III),

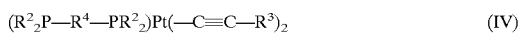  (IV)

and

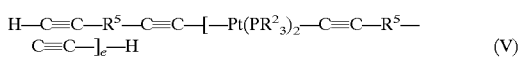  (V)

where $R^2$ may be identical or different and are monovalent, substituted or unsubstituted hydrocarbon radicals having from 1 to 24 carbon atoms, halogen atoms, hydrogen atoms, hydroxy radicals, —CN or —SCN, which are bound to phosphorus either directly or via oxygen, nitrogen or sulfur, $R^3$ are identical or different monovalent, substituted or unsubstituted hydrocarbon radicals having from 1 to 24 carbon atoms, $R^4$ are identical or different divalent, substituted or unsubstituted hydrocarbon radicals having from 1 to 14 carbon atoms, $R^5$ are identical or different divalent, substituted or unsubstituted hydrocarbon radicals having from 1 to 24 carbon atoms, and e is an integer greater than or equal to 1.

If the radicals $R^2$, $R^3$, $R^4$ and $R^5$ are substituted hydrocarbon radicals, preferred substituents are halogen atoms such as F, Cl, Br and I, cyano radicals and —$OR^6$ groups, where $R^6$ may be identical or different and are each a hydrogen atom or a monovalent hydrocarbon radical having from 1 to 20 carbon atoms.

The compositions of the invention can be one-component organopolysiloxane compositions or else two-component organopolysiloxane compositions. In the latter case, the two components of the composition of the invention can contain all constituents in any combination, generally with the proviso that one component does not simultaneously contain siloxanes having an aliphatic multiple bond, siloxanes containing Si-bonded hydrogen and catalyst, i.e. the constituents (A), (B) and (D) or (C) and (D) are essentially not present together. The compositions of the invention are preferably one-component compositions.

The compounds (A) and (B) or (C) used in the compositions of the invention are, as is known, selected so that crosslinking is possible. Thus, for example, but not by limitation, compound (A) may have at least two aliphatically unsaturated radicals and siloxane (B) may have at least three Si-bonded hydrogen atoms, or compound (A) may have at least three aliphatically unsaturated radicals and siloxane (B) may have at least two Si-bonded hydrogen atoms. Alternatively, in place of compound (A) and (B), use may be made of siloxane (C) which has aliphatically unsaturated radicals and Si-bonded hydrogen atoms in the above-mentioned ratios.

The compounds (A) used according to the invention can be either silicon-free organic compounds having preferably at least two aliphatically unsaturated groups, or organosilicon compounds having preferably at least two aliphatically unsaturated groups. Examples of organic compounds which can be used as component (A) in the compositions of the invention are 1,3,5-trivinylcyclohexane, 2,3-dimethyl-1,3-butadiene, 7-methyl-3-methylene-1,6-octadiene, 2-methyl-1,3-butadiene, 1,5-hexadiene, 1,7-octadiene, 4,7-methylene-4,7,8,9-tetrahydroindene, methylcyclopentadiene, 5-vinyl-2-norbornene, bicyclo[2.2.1]hepta-2,5-diene, 1,3-diisopropenylbenzene, polybutadiene containing vinyl groups, 1,4-divinylcyclohexane, 1,3,5-triallylbenzene, 1,3,5-trivinylbenzene, 1,2,4-trivinylcyclohexane, 1,3,5-triisopropenylbenzene, 1,4-divinylbenzene, 3-methylhepta-1,5-diene, 3-phenylhexa-1,5-diene, 3-vinylhexa-1,5-diene and 4,5-dimethyl-4,5-diethylocta-1,7-diene, N,N'-methylenebis(acrylamide), 1,1,1-tris(hydroxymethyl) propane triacrylate, 1,1,1-tris(hydroxymethyl)propane trimethacrylate, tripropylene glycol diacrylate, diallyl ether, diallylamine, diallyl carbonate, N,N'-diallylurea, triallylamine, tris(2-methylallyl)amine, 2,4,6-triallyloxy-1,3,5-triazine, triallyl-s-triazine-2,4,6(1H,3H,5H)-trione, diallyl malonate, polyethylene glycol diacrylate, polyethylene glycol dimethacrylate and poly(propylene glycol) methacrylate.

However, the silicone compositions of the invention preferably comprise, as constituent (A), an aliphatically unsaturated organosilicon compound, where all aliphatically unsaturated organosilicon compounds used hitherto in addition-crosslinking compositions can be used, for example silicone block copolymers having urea segments, silicone block copolymers having amide segments and/or imide segments and/or esteramide segments and/or polystyrene segments and/or silarylene segments and/or carborane segments and silicone graft copolymers containing ether groups.

As organosilicon compounds (A) which have SiC-bonded radicals containing aliphatic carbon—carbon multiple bonds, preference is given to using linear or branched organopolysiloxanes comprising units of the formula

$$R_a R^1_b SiO_{(4-a-b)/2} \qquad (I)$$

where

R may be identical or different and are each an organic radical which is free of aliphatic carbon—carbon multiple bonds, $R^1$ may be identical or different and are each a monovalent, substituted or unsubstituted, SiC-bonded hydrocarbon radical containing aliphatic carbon—carbon multiple bonds, a is 0, 1, 2 or 3 and b is 0, 1 or 2, with the proviso that the sum a+b is less than or equal to 3 and at least two radicals $R^1$ are present per molecule.

Radicals R can be monovalent or polyvalent radicals, where polyvalent radicals such as divalent, trivalent and tetravalent radicals then connect a plurality, for example two, three or four, of siloxy units of the formula (I) to one another.

R includes the monovalent radicals —F, —Cl, —Br, —$OR^6$, —CN, —SCN, —NCO, —$NO_2$ and SiC-bonded, substituted or unsubstituted hydrocarbon radicals which may be interrupted by oxygen atoms or the group —C(O)—, and also divalent radicals bound to Si at both ends in accordance with formula (I).

If the radical R is an SiC-bonded, substituted hydrocarbon radical, preferred substituents are halogen atoms, phosphorus-containing radicals, cyano radicals, —$OR^6$, —$NR^6$—, —$NR^6_2$, —$NR^6$—C(O)—$NR^6_2$, —C(O)—$NR^6_2$, —C(O)—$R^6$, —C(O)$OR^6$, —$SO_2$—Ph and —$C_6F_5$, where $R^6$ is as defined above and Ph is a phenyl radical.

Examples of radicals R are alkyl radicals such as the methyl, ethyl, n-propyl, iso-propyl, n-butyl, iso-butyl, tert-butyl, n-pentyl, iso-pentyl, neo-pentyl and tert-pentyl radicals; hexyl radicals such as the n-hexyl radical; heptyl radicals such as the n-heptyl radical; octyl radicals such as the n-octyl radical and iso-octyl radicals such as the 2,2,4-trimethylpentyl radical; nonyl radicals such as the n-nonyl radical; decyl radicals such as the n-decyl radical; dodecyl radicals such as the n-dodecyl radical; and octadecyl radicals such as the n-octadecyl radical; cycloalkyl radicals such as the cyclopentyl, cyclohexyl, cycloheptyl and methylcyclohexyl radicals; aryl radicals such as the phenyl, naphthyl, anthryl and phenanthryl radicals; alkaryl radicals such as o-, m-, p-tolyl radicals, xylyl radicals and ethylphenyl radicals; and aralkyl radicals such as the benzyl radical and the α- and β-phenylethyl radicals.

Examples of substituted radicals R are haloalkyl radicals such as the 3,3,3-trifluoro-n-propyl radical, the 2,2,2',2',2'-hexafluoroisopropyl radical, the heptafluoroisopropyl radical, haloaryl radicals such as the o-, m- and p-chlorophenyl radicals;

—(CH$_2$)$_n$—N(R$^6$)C(O)NR$^6$$_2$, —(CH$_2$)$_n$—C(O)NR$^6$$_2$, —(CH$_2$)$_n$—C(O)R$^6$, —(CH$_2$)$_n$—C(O)OR$^6$, —(CH$_2$)$_n$—C(O)—(CH$_2$)$_m$—C(O)CH$_3$, —(CH$_2$)$_n$—O—CO—R$^6$, —(CH$_2$)$_n$—NR$^6$—(CH$_2$)$_m$—NR$^6$$_2$, —(CH$_2$)$_n$—O—(CH$_2$)$_m$—CH(OH)—CH$_2$OH, —(CH$_2$)$_n$—(OCH$_2$CH$_2$)$_m$—OR$^6$, —(CH$_2$)$_n$—SO$_2$—Ph and —(CH$_2$)$_n$—O—C$_6$F$_5$, where R$^6$ is as defined above, n and m are identical or different integers in the range from 0 to 10 and Ph is the phenyl radical.

Examples of divalent radicals R which are bound to Si at both ends in accordance with formula (I) are those which are derived from the monovalent examples mentioned above for radical R by formation of an additional bond by replacement of a hydrogen atom. Examples of such radicals are —(CH$_2$)$_n$—, —CH(CH$_3$)—, —C(CH$_3$)$_2$—, —CH(CH$_3$)—CH$_2$—, —CH(Ph)—CH$_2$—, —C(CF$_3$)$_2$—, —(CH$_2$)$_n$—C$_6$H$_4$— (CH$_2$)$_n$—, —(CH$_2$)$_n$—C$_6$H$_4$—C$_6$H$_4$—(CH$_2$)$_n$—, —(CH$_2$O)$_m$—, —(CH$_2$CH$_2$O)$_m$—, —(CH$_2$)$_n$—O$_x$—C$_6$H$_4$—SO$_2$—C$_6$H$_4$—O$_x$—(CH$_2$)$_n$—, where x is 0 or 1, m and n are as defined above, and Ph is a phenyl radical.

The radical R is preferably a monovalent, SiC-bonded, substituted or unsubstituted hydrocarbon radical which is free of aliphatic carbon—carbon multiple bonds and has from 1 to 18 carbon atoms, particularly preferably a monovalent, SiC-bonded hydrocarbon radical which is free of aliphatic carbon—carbon multiple bonds and has from 1 to 6 carbon atoms, in particular the methyl or phenyl radical.

Radicals R$^1$ can be any groups which are capable of undergoing an addition reaction (hydrosilylation) with an SiH-functional compound. If radical R$^1$ is an SiC-bonded, substituted hydrocarbon radical, preferred substituents are halogen atoms, cyano radicals and —OR$^6$, where R$^6$ is as defined above.

Radicals R$^1$ are preferably alkenyl and alkynyl groups having from 2 to 16 carbon atoms, e.g. vinyl, allyl, methallyl, 1-propenyl, 5-hexenyl, ethynyl, butadienyl, hexadienyl, cyclopentenyl, cyclopentadienyl, cyclohexenyl, vinylcyclohexylethyl, divinylcyclohexylethyl, norbornenyl, vinylphenyl and styryl radicals, with particular preference being given to using vinyl, allyl and hexenyl radicals.

The molecular weight of the constituent (A) can vary within wide limits, for instance from 10$^2$ to 10$^6$ g/mol. Thus, the constituent (A) can be, for example, a relatively low molecular weight alkenyl-functional oligosiloxane such as 1,2-divinyltetramethyldisiloxane, but it may also be a polydimethylsiloxane high polymer having Si-bonded vinyl groups at the ends or laterally along the chain, e.g. one having a molecular weight of 10$^5$ g/mol (number average determined by means of NMR). The structure of the molecules forming the constituent (A) is not fixed. In particular, the structure of a high molecular weight, i.e. oligomeric or polymeric, siloxane may be linear, cyclic, branched or even resin-like, or network-like. Linear and cyclic polysiloxanes are preferably made up of units of the formulae R$_3$SiO$_{1/2}$, R$^1$R$_2$SiO$_{1/2}$, R$^1$RSiO$_{2/2}$ and R$_2$SiO$_{2/2}$, where R and R$^1$ are as defined above. Branched and network-like polysiloxanes further comprise trifunctional and/or tetrafunctional units, preferably ones of the formulae RSiO$_{3/2}$, R$^1$SiO$_{3/2}$ and SiO$_{4/2}$. Of course, it is also possible to use mixtures of different siloxanes which satisfy the criteria of constituent (A).

As component (A), particular preference is given to using vinyl-functional, essentially linear polydiorganosiloxanes having a viscosity of from 0.01 to 500,000 Pa·s, particularly preferably from 0.1 to 100,000 Pa·s, the viscosity in each case measured at 25° C.

As organosilicon compounds (B), it is possible to use all hydrogen-functional organosilicon compounds which have also been used hitherto in addition-crosslinking compositions.

As organopolysiloxanes (B) which have Si-bonded hydrogen atoms, preference is given to using linear, cyclic or branched organopolysiloxanes comprising units of the formula $$R_c H_d SiO_{(4-c-d)/2} \quad \text{(II)}$$

where

R may be identical or different and are as defined above, c is 0, 1, 2 or 3 and d is 0, 1 or 2, with the proviso that the sum of c+d is less than or equal to 3 and at least two Si-bonded hydrogen atoms are present per molecule.

The organopolysiloxane (B) used according to the invention preferably contains from 0.04 to 1.7 percent by weight of Si-bonded hydrogen, based on the total weight of the organopolysiloxane (B).

The molecular weight of the constituent (B) can likewise vary within wide limits, for instance from 10$^2$ to 10$^6$ g/mol. Thus, the constituent (B) can be, for example, a relatively low molecular weight SiH-functional oligosiloxane such as tetramethyldisiloxane, but it can also be a polydimethylsiloxane high polymer having SiH groups at the ends or laterally along the chain or a silicone resin containing SiH groups. The structure of the molecules forming the constituent (B) is not fixed either; in particular, the structure of a high molecular weight, i.e. oligomeric or polymeric, SiH-containing siloxane can be linear, cyclic, branched or else resin-like, network-like. Linear and cyclic polysiloxanes are preferably made up of units of the formulae R$_3$SiO$_{1/2}$, HR$_2$SiO$_{1/2}$, HRSiO$_{2/2}$ and R$_2$SiO$_{2/2}$, where R is as defined above Branched and network-like polysiloxanes further comprise trifunctional and/or tetrafunctional units, preferably ones of the formulae RSiO$_{3/2}$, HSiO$_{3/2}$ and SiO$_{4/2}$. Of course, it is also possible to use mixtures of different siloxanes which satisfy the criteria of constituent (B). In particular, the molecules forming constituent (B) can also contain aliphatically unsaturated groups in addition to the obligatory SiH groups. Particular preference is given to using low molecular weight SiH-functional compounds such as tetrakis(dimethylsiloxy)silane and tetramethylcyclotetrasiloxane, and also high molecular weight, SiH-containing siloxanes such as poly(hydrogenmethyl)siloxane and poly(dimethylhydrogenmethyl)siloxane having a viscosity at 25° C. of from 10 to 10,000 mPa·s, or analogous SiH-containing compounds in which some of the methyl groups are replaced by 3,3,3-trifluoropropyl or phenyl groups.

Constituent (B) is preferably present in the overall, crosslinkable silicone compositions of the invention in such an amount that the molar ratio of SiH groups to aliphatically unsaturated groups is from 0.1 to 20, particularly preferably from 0.1 to 5.0.

The components (A) and (B) used according to the invention are commercial products or can be prepared by methods which are well known in chemistry.

In place of components (A) and (B), the compositions of the invention may comprise organopolysiloxanes (C) which have aliphatic carbon—carbon multiple bonds and Si-bonded hydrogen atoms, but this is not preferred.

If siloxanes (C) are used, they are preferably ones comprising units of the formulae $$R_f SiO_{4-f/2}, R_g R^1 SiO_{3-g/2} \text{ and } R_h HSiO_{3-h/2}$$

where R and R$^1$ are as defined above, f is 0, 1, 2 or 3, g is 0, 1 or 2 and h is 0, 1 or 2, with the proviso that at least two radicals $R^1$ and at least two Si-bonded hydrogen atoms are present per molecule.

Examples of organopolysiloxanes (C) are ones comprising $SiO_{4/2}$, $R_3SiO_{1/2}$, $R_2R^1SiO_{1/2}$ and $R_2HSiO_{1/2}$ units, known as MQ resins, where these resins may further comprise $RSiO_{3/2}$ and $R_2SiO$ units, and also linear organopolysiloxanes consisting essentially of $R_2R^1SiO_{1/2}$, $R_2SiO$ and RHSiO units where R and $R^1$ are as defined above.

The organopolysiloxanes (C) preferably have an average viscosity of from 0.01 to 500,000 Pa·s, particularly preferably from 0.1 to 100,000 Pa·s, in each case measured at 25° C.

Organopolysiloxanes (C) can be prepared by methods which are well known in chemistry.

The platinum catalyst (D) of the formula (III), (IV) or (V) which is used according to the invention has an approximately square-planar arrangement of ligands around the platinum, which is why cis/trans isomers are possible. Both the cis and the trans compounds are subject matter of the present invention. In platinum catalysts of the formula (V), e is preferably an integer from 1 to 50, particularly preferably fro m 1 to 10.

Examples of phosphorus compounds $PR^2_3$ are trialkylphosphines such as trimethylphosphine, triethylphosphine, tripropylphosphine, triisopropylphosphine, tri-n-butylphosphine, tri-tert-butylphosphine, tricyclohexylphosphine and the like; arylphosphines such as triphenylphosphine, tribenzylphosphine, dimethylphenylphosphine, diethylphenylphosphine, dicyclohexylphenylphosphine, dichlorophenylphosphine, methyldiphenylphosphine, ethyldiphenylphosphine, diphenylpropylphosphine, isopropenyldiphenylphosphine, butyldiphenylphosphine, phenylphosphine, diphenyltolylphosphine, tri-o-, -m- and -p-tolylphosphine. It is likewise possible to use any phosphites as $PR^2_3$, for example trialkyl phosphites such as trimethyl phosphite, triethyl phosphite, triisopropyl phosphite, tri-n-butyl phosphite, tri-tert-butyl phosphite, triisodecyl phosphite, tris(tridecyl) phosphite and the like; aryl phosphites such as triphenyl phosphite, tri-o-, -m- and -p-tolyl phosphite, tris(isopropylphenyl) phosphite, tris(tert-butylphenyl) phosphite, tris(2,4-di-tert-butylphenyl) phosphite, tris(2,6-dimethylphenyl) phosphite, tris(nonylphenyl) phosphite, benzyl diethyl phosphite and the like; phosphinous esters such as methyl diphenylphosphinite, ethyl diphenylphosphinite, phenyl diphenylphosphinite and the like; phosphonous esters such as dimethyl benzenephosphonite, diethyl benzenephosphonite, diphenyl benzenephosphonite, dimethyl ethylphosphonite, ethyl benzenephosphonite and the like; substituted derivatives of the abovementioned radicals, e.g. diphenyl(pentahalophenyl) phosphine, tris(chlorophenyl)-phosphine, tris(fluorophenyl) phosphine, bis(pentahalo-phenyl)phenylphosphine, tris(pentahalophenyl)-phosphine, tris(2-chloroethyl) phosphite, tris(2,2,2-trifluoroethyl) phosphite, tris(chloropbenyl) phosphite, tris(2-cyanoethyl)phosphine and the like.

Examples of phosphorus compounds $R^2_2P-R^4-PR^2_2$ are bis(diphenylphosphino)methane, 1,2-bis(dimethylphosphino)ethane, 1,3-bis(diphenylphosphino)propane, 1,2-bis(diphenylphosphino)propane, cis-1,2-bis(diphenylphosphino)ethylene, tetraethyl pyrophosphite, tetrabenzyl pyrophosphite and the like.

$R^3$ is determined by the alkyne H—C≡C—$R^3$ used in the catalyst synthesis. Examples of alkynes are acetylene, (trimethylsilyl)acetylene, (triethylsilyl)acetylene, alkynes containing alkyl groups, e.g. 1-propyne, 1-butyne, 3,3-dimethyl-1-butyne, 1-pentyne, 1-hexyne, cyclohexylacetylene, 1-heptyne, 1-octyne, 1-nonyne, 1-decyne, 1-dodecyne and the like; alkynes containing alkene groups, e.g. 2-methyl-1-buten-3-yne, 1-ethynylcyclohexene, monovinylacetylene and the like; OH-substituted alkynes such as propargyl alcohol, 3-butyn-2-ol, 2-methyl-3-butyn-2-ol, 3-methyl-1-pentyn-3-ol, 4-pentyn-1-ol, 4-pentyn-2-ol, 4-pentyn-3-ol, 5-hexyn-1-ol, 3,5-dimethyl-1-hexyn-3-ol, 1-ethynyl-1-cyclohexanol, 3-nonyn-1-ol, 1-octyn-3-ol and the like; alkynes containing aromatic groups, e.g. phenylacetylene, 4-ethynyltoluene, 3-phenyl-1-propyne, 2-phenyl-3-butyn-2-ol and the like; alkynes containing ether groups, e.g. alkyl ethers of the abovementioned OH-substituted alkynes, ethyl ethynyl ether, methyl propargyl ether and the like; alkynes containing ester groups, e.g. methyl propiolate, ethyl propiolate, methyl 4-pentynoate, acetaldehyde ethyl propargyl acetal and the like; alkynes containing amino groups, e.g. propargylamine, 1-ethynylcyclohexylamine, 1,1-dimethylpropargylamine, N-methylpropargylamine, N,N-dimethylpropargylamine, N-benzyl-N-methylpropargylamine, 2-ethynylpyridine and the like; halogen-substituted alkynes such as propargyl chloride, propargyl bromide, 5-chloro-1-pentyne and the like.

Examples of alkynes H—C≡C—$R^5$—C≡C—H are 1,3-butadiyne, 1,4-pentadiyne, 1,5-hexadiyne, 1,6-heptadiyne, 1,7-octadiyne, 1,8-nonadiyne, diethynylbenzene, dipropargylamine, dipropargyl ether, 9,10-diethynylanthracene, diethynyldimethylsilane, 1,3-diethynyl-1,1,3,3-tetramethyldisiloxane, 1,2-diethynyl-1,1,2,2-tetramethyldisilane, polydimethylsiloxanes having ethynyl end groups and the like. The preparation of such polydimethylsiloxanes is generally known and described by, for example, O. G. Yarosh et al. in Izv. Akad.Nauk.SSSR, Ser. Khim. (1972), 2541–4.

Bis(alkynyl)bis(phosphine)platinum compounds and methods of preparing them have for some time been known to those skilled in the art. The preparation of platinum compounds of the formula (III) has been described, for example, by H. D. Empsall, B. L. Shaw, A. J. Stringer, J.ORGANOMET.CHEM. (1975), 94, 131–138, M. V. Russo, A. Furlani, J.ORGANOMET. CHEM. (1979), 165, 101–105, I. Collamati, A. Furlani, J.ORGANOMET.CHEM. (1969), 17, 457–461, A. Furlani, P. Bicev, M. V. Russo, P. Carusi, J.ORGANOMET.CHEM. (1971) 29, 321–327, K. Sonogashira et al., J.ORGANOMET.CHEM. (1978) 145, 101–108, A. Furlani, P. Carusi, M. V. Russo, J.ORGANOMET.CHEM. (1976), 116, 113–122 and A. Furlani et al., J. C. S. DALTON (1984) 2197–2206. The preparation of platinum compounds of the formula (V) has been described, for example, by K. Sonogashira, S. Takahashi, N. Hagihara, MMACROMOLECULES (1977) 879–880 and S. Kotani, K. Shiina, K. Sonogashira, APPL.ORGANOMET.CHEM, (1991), 5, 417–425. The preparation of platinum compounds of the formula (IV) has been described, for example, by J. F. Almeida, A. Pidcock, J.ORGANOMET.CHEM. (1981) 209, 415–423 and J. Fornies, M. A. Gomez-Saso, E. Lalinde, F. Martinez, M. T. Moreno, ORGANOMETALLICS (1992), 11, 2873–2883. Platinum complexes used according to the invention which have not yet been described explicitly can be prepared by methods analogous to those reported in the above-cited literature references.

The platinum catalyst (D) used according to the invention is preferably a bis(alkynyl)bis(triphenylphosphine)platinum complex, with particular preference being given to trans-$(Ph_3P)_2Pt[—C≡CC_6H_{10}(OH)]_2$, trans-$(Ph_3P)_2Pt[—C≡C—Ph]_2$ trans-$(Ph_3P)_2Pt(—C≡C—SiMe_3)_2$.

As platinum catalyst (D) to be used according to the invention, it is possible to employ one compound or a mixture of compounds of the type described for (D).

The amount of platinum catalyst (D) used according to the invention depends on the desired crosslinking rate and the respective use as well as economic considerations. The compositions of the invention comprise platinum catalysts (D) in such amounts that a platinum content of preferably from 0.05 to 500 ppm by weight (=parts by weight per million parts by weight), more preferably from 0.5 to 100 ppm by weight, and in particular from 1 to 50 ppm by weight, in each case based on the total weight of the composition, results.

Apart from the components (A) to (D), the curable compositions of the invention may further comprise all further materials which have also been used hitherto for preparing addition-cros slinking compositions.

Examples of reinforcing fillers which can be used as a component (E) in the compositions of the invention are pyrogenic or precipitated silicas having BET surface areas of at least 50 $m^2/g$, and also furnace black and acetylene black, with pyrogenic and precipitated silicas having BET surface areas of at least 50 $m^2/g$ being preferred. The silica fillers mentioned can have hydrophilic character or can have been hydrophobicized by known methods. When mixing-in hydrophilic fillers, the addition of a hydrophobicizing agent is generally necessary. The content of actively reinforcing filler (E) in the crosslinkable composition of the invention is in the range from 0 to 70% by weight, preferably from 0 to 50% by weight.

The silicone rubber composition of the invention can, if desired, further comprise, as constituent (F), further additives in an amount of up to 70% by weight, preferably from 0.0001 to 40% by weight. These additives can be, for example, inactive fillers, resin-like polyorganosiloxanes which are different from the siloxanes (A), (B) and (C), dispersants, solvents, adhesion promoters, pigments, dyes, plasticizers, organic polymers, heat stabilizers, etc. These include additives such as quartz flour, diatomaceous earth, clays, chalk, lithopones, carbon blacks, graphite, metal oxides, metal carbonates, metal sulfates, metal salts of carboxylic acids, metal dusts, fibers such as glass fibers, synthetic fibers, polymer powders, dyes, pigments, etc.

It is also possible for additives (G) which serve to adjust, in a targeted way, the processing time, start temperature and crosslinking rate of the compositions of the invention to be present. These inhibitors and stabilizers are very well known in the field of addition-crosslinking compositions. Examples of customary inhibitors are acetylenic alcohols such as 1-ethynyl-1-cyclohexanol, 2-methyl-3-butyn-2-ol and 3,5-dimethyl-1-hexyn-3-ol; polymethylvinylcyclosiloxanes such as 1,3,5,7-tetravinyltetramethyltetracyclosiloxane, low molecular weight silicone oils containing methylvinyl$SiO_{2/2}$ groups and/or $R_2$vinyl$SiO_{1/2}$ end groups, e.g. divinyltetramethyldisiloxane and/or tetravinyldimethyldisiloxane; trialkyl cyanurates; alkyl maleates such as diallyl maleate, dimethyl maleate and diethyl maleate; alkyl fumarates such as diallyl fumarate and diethyl fumarate; organic hydroperoxides such as cumene hydroperoxide, tert-butyl hydroperoxide and pinane hydroperoxide; organic peroxides; organic sulfoxides; organic amines, diamines and amides; phosphines and phosphites; nitriles; triazoles; diaziridines; and oximes. The action of these inhibitor additives (G) depends on their chemical structure, so that they have to be matched individually.

The inhibitor content of the compositions of the invention is preferably from 0 to 50,000 ppm, particularly preferably from 0 to 1,500 ppm, in particular from 5 to 600 ppm.

Most preferably, the compositions of the invention contain no constituents other than the components (A) to (G).

The organopolysiloxane compositions of the invention may, if necessary, be dissolved, suspended or emulsified in liquids.

The organopolysiloxane compositions of the invention can be prepared by known methods, for example by uniform mixing of the individual components. This can be done in any order, but preference is given to uniformly mixing the platinum catalyst (D) with a mixture of (A), (B) and, if desired, (E), (F) and (G). The platinum catalyst (D) used according to the invention can here be incorporated as a solid or as a solution in a suitable solvent or as a masterbatch in which it is uniformly mixed with a small amount of (A) or (A) together with (E).

The components (A) to (G) used according to the invention can each be a single type of such a component or else a mixture of at least two different types of such a component.

The novel compositions which can crosslink by addition of Si-bonded hydrogen onto aliphatic multiple bonds may be allowed to crosslink under the same conditions as the previously known compositions which can crosslink by a hydrosilylation reaction. Such conditions are preferably temperatures of from 100° C. to 200° C., particularly preferably of from 130° C. to 190° C., and a pressure of from 900 to 1100 hPa. However, it is also possible to employ higher or lower temperatures and pressures.

The present invention further provides moldings produced by crosslinking the compositions of the invention.

The compositions of the invention and the crosslinked products produced therefrom according to the invention can be used for all purposes for which organopolysiloxane compositions which can crosslink to give elastomers or elastomers themselves have also been used hitherto, for example as embedding compositions for electrical or electronic devices, as compositions for taking a cast, as coating compositions or for producing moldings, e.g. by injection molding, vacuum extrusion, extrusion, casting in molds and die pressing.

The crosslinkable compositions of the invention have the advantage that they can be prepared by a simple process using readily available starting materials, and have the further advantage that as one-component formulations they have good storage stability at 25° C. and ambient pressure and crosslink rapidly only at elevated temperature.

The silicone compositions of the invention have the advantage that in the case of a two-component formulation they provide, after mixing the two components, crosslinkable silicone composition which remain processable for a long period of time at 25° C. and ambient pressure (extremely long pot life) and crosslink rapidly only at elevated temperature.

In preparing the crosslicikable compositions o f the invention, it is of great advantage for the platinum catalyst (D) to be able to be incorporated easily.

The compositions of the invention have the further advantage that the platinum catalyst (D) can be prepared easily and in good yields.

In the examples described below, all parts and percentages are by weight unless otherwise indicated. If not indicated otherwise, the examples below are carried out at the pressure of the surrounding atmosphere, i.e. at about 1000 hPa, and at room temperature, i.e. at about 20° C., or at the temperature which is established on combining the reactants at room temperature without additional heating or cooling. All viscosities reported are at a temperature of 25° C. In the formulae, Vi represents a vinyl radical, Me represents a methyl radical, Bu represents a butyl radical and Ph represents a phenyl radical.

Preparation of the platinum catalysts to which reference is made in the following examples:

Catalyst 1

A suspension of 0.400 g (0.51 mmol) of cis-bis(triphenylphosphine)platinum(II) chloride, 0.150 g (1.21 mmol) of 1-ethynylcyclohexanol, 0.019 g of copper(I) iodide and 20 ml of diethylamine is stirred for 10 minutes. The mixture is subsequently refluxed for 30 minutes. After cooling to room temperature, the precipitate is separated from the solution and washed with ethanol. The product obtained is recrystallized from methylene chloride/ethanol and gives 0.406 g or an 83 % yield of product. Based on the method of preparation and the NMR spectra, the product is a platinum complex of the following formula:

trans-(Ph$_3$P)$_2$Pt[—C≡CC$_6$H$_{10}$(OH)]$_2$

Catalyst 2

Under a nitrogen atmosphere, 2.0 g (1.61 mmol) of tetrakis(triphenylphosphine)platinum(0) are suspended in 20 ml of diethyl ether and admixed with 0.180 g (3.21 mmol) of propargyl alcohol. The mixture is stirred overnight, the solvent is subsequently removed and the residue is suspended in 5 ml of propargyl alcohol and refluxed for 10 minutes. After cooling to room temperature, 10 ml of methanol are introduced as a layer on top of the solution, as a result of which a beige precipitate is gradually formed. This precipitate is separated from the solution and recrystallized from methylene chloride/methanol. This gives 0.840 g (63 % yield) of a colorless solid. Based on the method of preparation and the NMR spectra, the product is a platinum complex of the following formula:

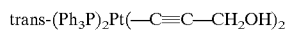

trans-(Ph$_3$P)$_2$Pt(—C≡C—CH$_2$OH)$_2$

Catalyst 3

The procedure described above for preparing catalyst 1 is repeated with the modification that 0.124 g (1.21 mmol) of phenylacetylene is used in place of the ethynylcyclohexanol. The product is not recrystallized. This gives 0.424 g (91% yield) of a yellow powder. Based on the method of preparation, the product is a platinum complex of the following formula:

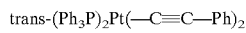

trans-(Ph$_3$P)$_2$Pt(—C≡C—Ph)$_2$

Catalyst 4

A suspension of 0.670 g (1.0 mmol) of cis-bis(tri-n-butylphosphine)platinum(II) chloride, 0.225 g (2.2 mmol) of phenylacetylene, 0.010 g of copper(I) iodide and 10 ml of diethylamine is stirred for 60 minutes. The mixture is subsequently refluxed for 30 minutes. After cooling to room temperature, the precipitate is separated from the solution and washed with methanol. This gives 0.640 g or an 80% yield of product. Based on the method of preparation and the NMR spectra, the product is a platinum complex of the following formula:

trans-(n-Bu$_3$P)$_2$Pt[—C≡C—Ph)$_2$

Catalyst 5

The procedure described above for the preparation of catalyst 1 is repeated with the modification that 0.120 g (1.21 mmol) of ethynyltrimethylsilane is used in place of the ethynylcyclohexanol. The product is washed with methanol. This gives 0.390 g (84% yield) of a light-yellow powder.

Based on the method of preparation and the NMR spectra, the product is a platinum complex of the following formula:

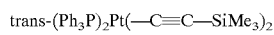

trans-(Ph$_3$P)$_2$Pt(—C≡C—SiMe$_3$)$_2$

EXAMPLE 1

50.0 g of a vinyldimethylsiloxy-terminated polydimethylsiloxane which has a viscosity of 20 Pa·s and 1.0 g of SiH crosslinker are homogeneously mixed by means of a model RE 162 stirrer from Janke & Kunkel IKA-Labortechnik. The SiH crosslinker is a copolymer of dimethylsiloxy and methylhydrogensiloxy and trimethylsiloxy units having a viscosity of 330 mPa·s and a content of Si-bonded hydrogen of 0.46% by weight. Subsequently, 2.5 mg (corresponding to a Pt content of 10 ppm based on the total composition) of catalyst 1 dissolved in 0.5 ml of methylene chloride are incorporated by stirring.

EXAMPLE 2

The procedure described in Example 1 is repeated with the modification that 3 mg of ethynylcyclohexanol are incorporated homogeneously by stirring prior to the addition of the catalyst.

EXAMPLE 3

The procedure described in Example 2 is repeated with the modification that 30 mg instead of 3 mg of ethynylcyclohexanol are employed.

EXAMPLE 4

The procedure described in Example 2 is repeated with the modification that 2.5 mg of 2,5-bis(tert-butylperoxy)-2,5-dimethylhexane (commercially available from Aldrich GmbH & Co. KG, Germany) are incorporated prior to the addition of the catalyst.

COMPARATIVE EXAMPLE 1

The procedure described in Example 3 is repeated with the modification that 10 ppm of platinum as platinum-divinyltetramethyldisiloxane complex in vinyl-terminated polydimethylsiloxane (commnercially available from ABCR GmbH & Co., Germany) are used as catalyst.

EXAMPLE 5

The procedure described in Example 3 is repeated with the modification that 25 mg of 2,5-bis(tert-butylperoxy)-2,5-dimethylhexane (commercially available from Aldrich GmbH & Co. KG) are incorporated prior to the addition of the catalyst and 2.1 mg of catalyst 2 (corresponding to a platinum content of 10 ppm based on the total silicone composition) are employed as catalyst.

EXAMPLE 6

255 parts by mass of a vinyldimethylsiloxy-terminated polydimethylsiloxane having a viscosity of 20 Pa·s are placed in a laboratory kneader, heated to 150° C. and admixed with 180 parts by mass of a hydrophobic pyrogenic silica having a specific surface area determined by the BET method of 300 m$^2$/g and a carbon content of 3.95 % by weight (commercially available under the name WACKER HDK® SKS 300 from Wacker-Chemie GmbH). This gives a stiff mass which is subsequently diluted with 165 parts by mass of the abovementioned polydimethylsiloxane. Volatile constituents are removed by kneading under reduced pressure (10 mbar) at 150° C. for one hour.

488.1 g of this base composition are mixed with 0.160 g of inhibitor, 10.95 g of SiH crosslinker, 0.40 g of tetrakis (vinyldimethylsiloxy)silane and 2.0 g of catalyst masterbatch on a roll mill at a temperature of 25° C. to give a homogeneous mass. Here, the inhibitor is ethynylcyclohexanol, the SiH crosslinker is a copolymer of dimethylsiloxy and methylhydrogensiloxy and trimethylsiloxy units having a viscosity of 320 mPa·s and a content of Si-bonded hydrogen of 0.48% by weight, and the catalyst masterbatch is a mixture of the abovementioned vinylpolydimethylsiloxane and catalyst 1 (platinum content=2.5 ppm based on the total composition).

COMPARATIVE EXAMPLE 2

The procedure described in Example 6 is repeated with the modification that 8 ppm of platinum are used as platinum-divinyltetramethyldisiloxane complex in vinyl-terminated polydimethylsiloxane (commercially available from ABCR GmbH & Co.).

EXAMPLE 7

The procedure described in Example 3 is repeated with the modification that 2.1 mg (corresponding to 10 ppm of platinum) of catalyst 4 are used in place of catalyst 1.

EXAMPLE 8

The procedure described in Example 6 is repeated with the modification that 5 ppm of platinum in the form of catalyst 3 dissolved in 0.5 ml of dichloromethane are used in place of catalyst 1.

EXAMPLE 9

The procedure described in Example 6 is repeated with the modification that 5 ppm of platinum in the form of catalyst 5 dissolved in 0.5 ml of dichloromethane are used in place of catalyst 1.

EXAMPLE 10

589.4 parts by mass of a vinyldimethylsiloxy-terminated polydimethylsiloxane having a Brabender plasticity of 630 mkp, corresponding to a mean molar mass of about 500,000 g/mol (number average determined by means of NMR), are mixed with 252.6 parts by mass of a hydrophobic pyrogenic silica having a BET surface area of 300 m$^2$/g and a carbon content of 3.95% by weight (commercially available under the name WACKER HDKO SKS 300 from Wacker-Chemie GmbH), which is added a little at a time, for 4 hours in a kneader to give a homogeneous composition.

500 g of this base composition are mixed with 0.02 g of inhibitor, 7.5 g of SiH crosslinker and 12.4 mg of catalyst 1 dissolved in 1 ml of dichloromethane on a roll mill at a temperature of 20° C. to give a homogeneous composition. Here, the inhibitor is ethynylcyclohexanol and the SiH crosslinker is a copolymer of dimethylsiloxy and methylhydrogensiloxy and trimethylsiloxy units having a viscosity of 310 mPa·s and a content of Si-bonded hydrogen of 0.46% by weight.

EXAMPLE 11

The procedure described in Example 10 is repeated with the modification that 12.0 mg of catalyst 3 are used in place of catalyst 1.

EXAMPLE 12

The thermal curing properties of the silicone compositions prepared in Examples 1, 2, 3, 4, 5 and 7 and in Comparative Example 1 are measured by means of a Dynamic Analyzer RDA II from Rheometrics using a heating curve from 30 to 200° C. and a heating rate of 5° C./minute. To determine the storage life quantitatively, the formulations prepared are stored at room temperature and 50° C., with the number of days until the viscosity has reached twice the initial value being determined. The results of the measurements are shown in Table 1.

The thermal curing properties of the silicone compositions of Examples 6, 8, 9, 10 and 11 and of Comparative Example 2 are measured using a Goettfert Elastograph. To determine the storage life quantitatively, the formulations prepared are stored at room temperature and 50° C., with the number of days until the viscosity has reached twice the initial value being determined. The results of the measurements are shown in Table 2.

TABLE 1

|  | Ex. 1 | Ex. 2 | Ex. 3 | Ex. 4 | C. Ex. 1 | Ex. 5 | Ex. 7 |
|---|---|---|---|---|---|---|---|
| a$_T$' [° C.] | 136.8 | 141.3 | 150.0 | 141.5 | 95.4 | 143.7 | 151.7 |
| t' (a$_T$') [min] | 21.36 | 22.26 | 24.00 | 22.30 | 13.08 | 22.74 | 24.34 |
| t$_{75}$' [min] | 24.94 | 27.58 | 27.58 | 24.82 | 16.81 | 24.90 | 27.60 |
| Storage at RT | >191 d | >267 d | >267 d | >334 d | 12 d | 281 d | >186 d |
| Storage at 50° C. | 43 d | 65 d | 176 d | 74 d | 1 d | — | >186 d |

Legend for Table 1:
d    days
min    minutes
s    seconds
a$_T$'    start temperature
t'(a$_T$')    time until crosslinking commences
t$_{75}$'    time until 75% of the maximum torque is reached

TABLE 2

|  | Ex. 6 | C. Ex. 2 | Ex. 8 | Ex. 9 | Ex. 10 | Ex. 11 |
|---|---|---|---|---|---|---|
| a$_T$ [° C.] | 150.3 | 115.8 | 155.7 | 152.0 | 131.6 | 137.2 |
| t$_{90}$ [S] | 66 | 29 | 88 | 69 | 55 | 62 |
| Storage at RT | >180 d | 15 d | >180 d | 146 d | >109 d | >109 d |
| Storage at 50° C. | 89 d | 3 d | 94 d | 37 d | 63 d | 67 d |

Legend for Table 2:
d    days
min    minutes
s    seconds
a$_T$    start temperature; it is determined at a heating rate of 10° C./min. The temperature which corresponds to 4% of the maximum torque is taken as the start temperature.
t$_{90}$    the value of t$_{90}$ is determined in accordance with DIN 53529-3. The time from the commencement of curing to 90% (t$_{90}$) of the maximum torque is determined at 180° C.

What is claimed is:

1. A curable organopolysiloxane composition, comprising: an addition-crosslinkable organopolysiloxane component, comprising
    (A) compounds having radicals containing aliphatic carbon—carbon multiple bonds,
    (B) organopolysiloxanes containing Si-bonded hydrogen atoms, and/or
    (C) organopolysiloxanes having SiC-bonded radicals containing aliphatic carbon—carbon multiple bonds and Si-bonded hydrogen atoms, and a catalyst component comprising (D) a platinum catalyst selected from the group consisting of

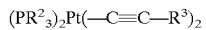 (III),

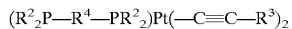 (IV)

and

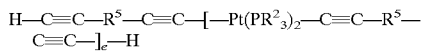 (V)

where

R$^2$ may be identical or different and are monovalent, substituted or unsubstituted hydrocarbon radicals having from 1 to 24 carbon atoms, halogen atoms, hydrogen atoms, hydroxy radicals, —CN or —SCN, which are bound to phosphorus either directly or via oxygen, nitrogen or sulfur, R$^3$ are identical or different monovalent, substituted or unsubstituted hydrocarbon radicals having from 1 to 24 carbon atoms, R$^4$ are identical or different divalent, substituted or unsubstituted hydrocarbon radicals having from 1 to 14 carbon atoms, R$^5$ are identical or different divalent, substituted or unsubstituted hydrocarbon radicals having from 1 to 24 carbon atoms, and e is an integer greater than or equal to 1.

2. A curable organopolysiloxane composition as claimed in claim 1, wherein constituent (A) is an aliphatically unsaturated organosilicon compound.

3. A curable organopolysiloxane composition as claimed in claim 1, wherein the organosilicon compounds (A) used are linear or branched organopolysiloxanes comprising units of the formula $$R_a R^1_b SiO_{(4-a-b)/2}$$ (I)

where

R may be identical or different and are each an organic radical which is free of aliphatic carbon—carbon multiple bonds, R$^1$ may be identical or different and are each a monovalent, substituted or unsubstituted, SiC-bonded hydrocarbon radical containing aliphatic carbon—carbon multiple bonds, a is 0, 1, 2 or 3 and b is 0, 1 or 2, with the proviso that the sum a+b is less than or equal to 3 and at least two radicals R$^1$ are present per molecule.

4. A curable organopolysiloxane composition as claimed in claim 3, wherein the radical R is a monovalent, SiC-bonded hydrocarbon radical which is free of aliphatic carbon—carbon multiple bonds and has from 1 to 6 carbon atoms.

5. A curable organopolysiloxane composition as claimed in claim 1, wherein the organopolysiloxanes (B) are linear, cyclic or branched organopolysiloxanes comprising units of the formula

 (II)

where

R may be identical or different and are as defined above, c is 0, 1, 2 or 3 and d is 0, 1 or 2, with the proviso that the sum of c+d is less than or equal to 3 and at least two Si-bonded hydrogen atoms are present per molecule.

6. A curable organopolysiloxane composition as claimed in claim 2, wherein the organopolysiloxanes (B) are linear, cyclic or branched organopolysiloxanes comprising units of the formula

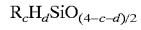 (II)

where

R may be identical or different and are as defined above, c is 0, 1, 2 or 3 and d is 0, 1 or 2, with the proviso that the sum of c+d is less than or equal to 3 and at least two Si-bonded hydrogen atoms are present per molecule.

7. A curable organopolysiloxane composition as claimed in claim 3, wherein the organopolysiloxanes (B) are linear, cyclic or branched organopolysiloxanes comprising units of the formula

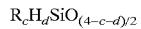 (II)

where

R may be identical or different and are as defined above, c is 0, 1, 2 or 3 and d is 0, 1 or 2, with the proviso that the sum of c+d is less than or equal to 3 and at least two Si-bonded hydrogen atoms are present per molecule.

8. A curable organopolysiloxane composition as claimed in claim 4, wherein the organopolysiloxanes (B) are linear, cyclic or branched organopolysiloxanes comprising units of the formula

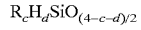 (II)

where

R may be identical or different and are as defined above, c is 0, 1, 2 or 3 and d is 0, 1 or 2, with the proviso that the sum of c+d is less than or equal to 3 and at least two Si-bonded hydrogen atoms are present per molecule.

9. A curable organopolysiloxane composition as claimed in claim 1, wherein the catalyst (D) used comprises a bis(alkynyl)bis(triphenylphosphine)platinum complex.

10. A curable organopolysiloxane composition as claimed in claim 2, wherein the catalyst (D) used comprises a bis(alkynyl)bis(triphenylphosphine)platinum complex.

11. A curable organopolysiloxane composition as claimed in claim 3, wherein the catalyst (D) used comprises a bis(alkynyl)bis(triphenylphosphine)platinum complex.

12. A curable organopolysiloxane composition as claimed in claim 4, wherein the catalyst (D) used comprises a bis(alkynyl)bis(triphenylphosphine)platinum complex.

13. A curable organopolysiloxane composition as claimed in claim 5, wherein the catalyst (D) used comprises a bis(alkynyl)bis(triphenylphosphine)platinum complex.

14. A molding produced by crosslinking a composition as claimed in claim 1.

15. A molding produced by crosslinking a composition as claimed in claim 1.

16. A molding produced by crosslinking a composition as claimed in claim 3.

* * * * *

UNITED STATES PATENT AND TRADEMARK OFFICE
CERTIFICATE OF CORRECTION

PATENT NO.    : 6,187,890 B1
DATED         : February 13, 2001
INVENTOR(S)   : Armin Fehn, et al.

It is certified that error appears in the above-identified patent and that said Letters Patent is hereby corrected as shown below:

<u>Column 16, claim 15,</u>
Line 63, delete "1" and insert -- 2 --.

Signed and Sealed this

Thirtieth Day of October, 2001

*Attest:*

*Attesting Officer*

NICHOLAS P. GODICI
*Acting Director of the United States Patent and Trademark Office*